(12) United States Patent
Krumme

(10) Patent No.: US 7,466,791 B2
(45) Date of Patent: Dec. 16, 2008

(54) DATA TRANSMISSION SYSTEM FOR COMPUTER TOMOGRAPHS

(75) Inventor: Nils Krumme, Feldafing (DE)

(73) Assignee: Schleifring und Apparatebau GmbH, Fuerstenfeldbruck (DE)

( * ) Notice: Subject to any disclaimer, the term of this patent is extended or adjusted under 35 U.S.C. 154(b) by 429 days.

(21) Appl. No.: 11/382,854

(22) Filed: May 11, 2006

(65) Prior Publication Data

US 2006/0256634 A1    Nov. 16, 2006

(30) Foreign Application Priority Data

May 12, 2005   (DE) ........................ 10 2005 022 825
Jul. 27, 2005   (DE) ........................ 10 2005 035 802

(51) Int. Cl.
*A61B 6/00*   (2006.01)
(52) U.S. Cl. ........................................ 378/15; 378/210
(58) Field of Classification Search ............... 378/4–20, 378/210

See application file for complete search history.

(56) References Cited

U.S. PATENT DOCUMENTS 6,433,631 B2    8/2002   Pearson, Jr. et al. .......... 329/611

FOREIGN PATENT DOCUMENTS

WO         03/028325        4/2003

*Primary Examiner*—Courtney Thomas
(74) *Attorney, Agent, or Firm*—Kevin L. Daffer; Daffer McDaniel, LLP

(57) ABSTRACT

A device for transmitting data between a rotating part and a stationary part of a computer tomograph, in which the rotating part comprises at least one data source; a conductor structure; and at least one first transmitter for energizing the conductor structure; and the stationary part comprises at least one data sink for evaluating data; at least one receiver; and a receiver coupler for tapping off signals from the conductor structure and supplying the signals to the at least one receiver; is improved to reduce radiation of high-frequency signals.

20 Claims, 2 Drawing Sheets

DATA TRANSMISSION SYSTEM FOR COMPUTER TOMOGRAPHS

PRIORITY CLAIM

This application claims priority to German Application No. 102005022825.9 filed May 12, 2005 and German Application No. 102005035802.0 filed Jul. 27, 2005.

BACKGROUND OF THE INVENTION

1. Field of the Invention

The invention relates to a data transmission system for transmitting data between a rotating part and a stationary part of a computer tomograph by means of directed radio transmission.

2. Description of the Prior Art

A device for data transmission in computer tomographs is described in the U.S. Pat. No. 6,433,631. A transmitter signal impinges upon a strip conductor line in a rotating part. A tap provided on a stationary part is provided to be movable while maintaining a short distance of an order of magnitude of about 1 mm from the strip conductor. Interference radiation can be strongly reduced by means of a differential configuration of a conductor structure.

With transmission systems of this kind it may happen that the entire arrangement radiates undesirably high noise levels into the surroundings. In order to render this radiation to be at least broadband, so that current EMC Standards can be complied with, it is suggested in WO 03/028325 that the data stream for transmission be coded with random numbers. For this, however, the data to be transmitted must be modified.

BRIEF SUMMARY OF THE INVENTION

It is the object of the invention to provide a data transmission system which, in comparison with prior art, exhibits a reduced emission of high-frequency signals, so that an undesired emission of high-frequency signals into the environment is reduced.

In accordance with the invention, this object is achieved in a device for transmitting data between a rotating part and a stationary part of a computer tomograph, in which the rotating part comprises at least one data source; a conductor structure; and at least one first transmitter for energizing the conductor structure; and the stationary part comprises at least one data sink for evaluating data; at least one receiver; and a receiver coupler for tapping off signals from the conductor structure and supplying the signals to the at least one receiver. According to one aspect of the invention, a resonance frequency of at least one of the rotating part and the conductor structure, and a spectral distribution of data of the at least one transmitter are matched to each other.

BRIEF DESCRIPTION OF THE DRAWINGS

In the following, the invention will be described by way of example, without limitation of the general inventive concept, on examples of embodiment and with reference to the drawings.

DETAILED DESCRIPTION OF PREFERRED EMBODIMENTS

Figure 1:
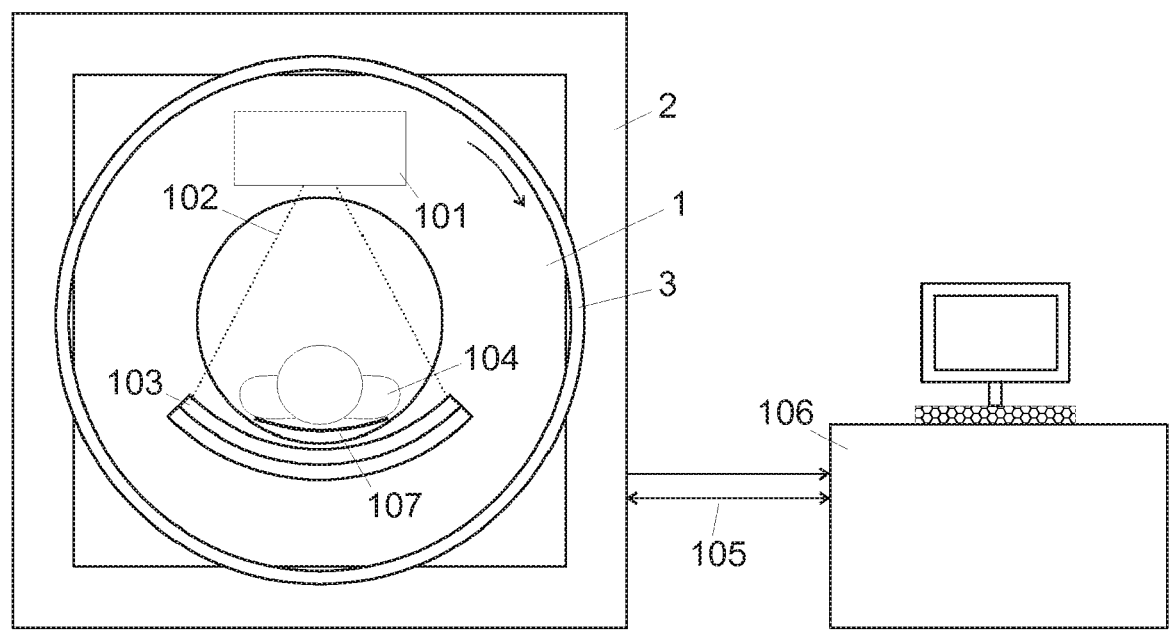
FIG. 1 schematically shows in a general form a computer tomograph.

A device in accordance with the invention for transmitting data between a rotating part and a stationary part of a computer tomograph comprises at least one data source on the rotating part, and at least one data sink for evaluating the data on the stationary part. Furthermore, at least one first transmitter and a conductor structure energized by the transmitter are provided in the rotating part. Energizing of the conductor structure is usually effected at its center. This energizing location divides the conductor structure into two parts of equal length extending in opposite directions from the feeding-in location. At least one receiver and a receiving coupler for energizing the receiver are provided in the stationary part. The receiving coupler taps off signals from the conductor structure.

It was shown by investigations that resonances may occur during operation of the arrangement, which are determined particularly by the configuration of the arrangement, and here especially by the configuration of the conductor structure. These have also been disclosed in MEINKE, GUNDLACH, "Taschenbuch der Hochfrequenztechnik" (Manual of High-Frequency Technology), published by Springer Verlag 1956, Chapter H24, "Rahmen-und Ringantennen" (Frame and Ring Antennas). In accordance with this, the conductor structure may be regarded as being a parasitic antenna.

In accordance with the invention, the configuration of the arrangement, and in particular the configuration of the conductor structure, and also the signals to be transmitted, are matched to each other.

Another improvement can be achieved by the transmitter signal being a random sequence that is distributed as uniformly as possible. This may be put into practice, for example, by folding an arbitrary data stream with a random sequence. It is also possible to transmit random numbers during transmission intervals instead of the usual interval patterns.

A particularly advantageous embodiment of the invention consists of the resonance frequency of the rotating part and/or the conductor structure being dimensioned to be in a frequency range in which the high-frequency energy emitted by a transmitter has a minimum value. This minimum value may be also any other arbitrary predetermined value.

Another advantageous embodiment of the invention consists of regions close to the conductor structure comprising a dielectric. By means of this dielectric, the resonance frequency of the conductor structure itself may be changed. The dielectric on the inside of the conductor structure has an only negligible effect on the resonance frequency of the conductor structure itself, because at resonance of the entire conductor structure, the potentials of the conductors and the screen surface are equal, and thus the dielectric on the inside of the conductor structure is field-free.

Another embodiment of the invention provides for the length of the conductor structure to be dimensioned so that it corresponds to a whole-number multiple of the half-wavelength of a frequency in which the high-frequency energy emitted by a transmitter has a minimum value. Particularly resonances at whole-number multiples of the half-wavelength that correspond to the length of the conductor structure occur preferably in this linear structure that is wound-off along the rotating part. This dimensioning is of particular advantage with ends of the conductor structure that are free, or coupled with each other capacitively. Similarly, an inductive or resistive coupling is also possible. For this, it is sufficient to connect together the ends of the screen surfaces. The screen and the conductor tracks may be connected together.

Another embodiment of the invention provides for the length of the conductor structure to be dimensioned so that it corresponds to a whole-number multiple of a quarter of the wavelength of a frequency in which the high-frequency energy emitted by a transmitter has a minimum value. This dimensioning is of particular advantage with short-circuited ends, i.e. interconnected ends, of the conductor structure.

Furthermore, it is of advantage when a loss-attended dielectric and/or ferromagnetic material is provided laterally of and/or below the conductor structure. With loss-attended materials of this kind, an additional attenuation can be achieved. A radiation of high-frequency signals is further reduced thereby.

It is of special advantage for the ends of the conductor structure to be attended by losses, and particularly to be connected to each other by an ohmic resistance. Hereby resonances of predetermined resonance frequencies, for example with multiples of one half of a wavelength corresponding to the length of the conductor structure, can be suppressed.

Another invention resides in folding the transmission signal of the transmitter with a bit sequence that is chosen so that its spectrum corresponds to a predetermined transmission spectrum. Thus, this bit sequence could be obtained, for example, from a predetermined transmission spectrum by an inverse spectral transformation such as an inverse Fourier transformation. In practice, the spectral distribution of the transmission signal is not exactly known in most cases. Assuming that a uniformly distributed sequence of the transmission signal is the case at least on average, an approximation to a predetermined spectrum can be obtained in this manner.

In another embodiment of the invention, the conductor structure is designed so that signals to be transmitted are satisfactorily conducted, but not radiated into the environment. Nevertheless, an occurrence of minor radiation usually cannot be avoided. Thus, known conductor structures usually form a closed circuit around a rotor or stator of a computer tomograph. This closed circuit as such is capable of resonance and radiates high-frequency energy preferably at its resonance frequency, inasmuch as a transmission signal contains appropriate spectral components. Now in accordance with the invention, this radiation can be captured and absorbed at least partly with an antenna, hereunder referred to as an absorber antenna. In accordance with the invention, optionally one, or a combination of a plurality of absorber antennas of this kind, may be used.

An absorber antenna in accordance with the invention may be a structural component of a slip ring. Thus for example, it may be made of a conductive plastic material, or designed to be a wire ring cast inside the slip ring. Similarly it may be a component part of an instrument frame, and may be manufactured, for example, in the form of a sheet of poorly conducting material. Similarly, it may be applied, for example in the form of a conducting coating such as of conductive varnish or the like, onto an insulating arrangement such as a cover.

It is of importance to the functioning of an absorber antenna for it to be coupled with one of the parasitic antennas that radiate undesired signals, which in the case of a computer tomograph is usually a conductor structure.

An especially advantageous embodiment of the invention consists in at least one of the absorber antennas being configured as a closed conductor loop that is preferably attended by losses. In this way, an absorber antenna corresponds to a frame antenna that is attended by losses. The bandwidth of an antenna may be increased by increasing the attenuation of the antenna. Frame antennas of this kind have a uniform field variation and correspond to the parasitic antennas which here consist of the conductor structure. Basically, however, dipole antennas may be used.

Another advantageous embodiment of the invention consists of at least one of the absorber antennas being designed to be optionally round or rectangular. Thus, for example, an absorber antenna in accordance with the invention may be disposed in the shape of a ring in the vicinity of the conductor structure. Similarly a rectangular absorber antenna may be disposed, for example, around a usually rectangular frame of a computer tomograph. An absorber antenna in accordance with the invention may be mounted optionally on a rotor, or on a stator, or on both parts.

Another embodiment of the invention provides for at least one of the absorber antennas to comprise at least one material that is attended by losses. A material of this kind that is attended by losses may be, for example, a resistance wire or also a resistance foil that is mounted preferably on a printed circuit board.

Another embodiment of the invention provides for at least one of the absorber antennas to comprise at least one attenuating resistor. Attenuating resistors are expedient when the absorber antenna itself is made of a material of poor attenuation, or of a material with insufficiently high attenuation. Furthermore, by an insertion of additional, or higher, or lower, attenuating resistors, an attenuation may be finely set and therewith matched to a respective case of application. In accordance with the invention, attenuating resistors are preferably connected in series, i.e. along an antenna. Alternatively, attenuating resistors may be connected also from one antenna in parallel with a reference face or a grounded surface.

Furthermore it is of advantage for at least one of the absorber antennas to comprise at least one series inductance and/or series capacity. Thus, an effective antenna length may be increased by means of series inductances, or reduced by means of series capacities. Matching of the resonance frequency to a frequency to be absorbed is possible with reactive elements of this kind. With this, it is also possible to configure the absorber antenna to have a shorter or longer radius than the conductor structure, because the frequency can be matched. Furthermore, an absorber antenna is of greater bandwidth than the self-resonance of the conductor structure and can therefore tolerate deviations.

It is of especial advantage when at least one of the absorber antennas comprises at least one parallel inductance and/or parallel capacity to a common ground. A matching by means of parallel inductances or parallel capacities may be effected in a similar manner to that described above, these being preferably connected to a common reference surface or ground.

Another embodiment comprises at least one of the absorber antennas that is tuned to a predetermined frequency. Thus, at least one of the absorber antennas is tuned to a frequency which is to be suppressed and which preferably corresponds to one of the resonance frequencies of a conductor structure.

Another embodiment of the invention provides a plurality of absorber antennas which are tuned to a plurality of predetermined frequencies. Thus, a matching to various resonance frequencies which may originate from different parts or different conductor structures is possible.

Another embodiment of the invention comprises at least one of the absorber antennas of rectangular shape. In this, the lengths of sides are whole-number multiples of λ/8 of the frequency to be attenuated.

Another embodiment of the invention comprises at least one of the absorber antennas of circular shape. In this, the circumference is a whole-number multiple of λ/4 of the frequency to be attenuated.

Another embodiment of the invention comprises at least one of the absorber antennas with a plurality of windings. The impedance of the antenna can be increased thereby.

A computer tomograph in accordance with the invention comprises a device in accordance with the above description.

In the present description, the direction of transmission has been chosen to be from the rotor to the stator, because this corresponds to the most frequent case of use. However, a transmission in the opposite direction, or even a bidirectional transmission, is equally possible.

FIG. 1 shows an example of a device according to the invention. A computer tomograph (CT scanner) consists of two main mechanical components. A stationary part 2 serves as a base and support of the entire instrument, in which a rotating part 1 revolves. A patient 104 is positioned on a berth 107 in an opening of the rotating part. An X-ray tube 101 and an oppositely disposed detector 103 are provided for scanning the patient by means of X-rays 102. The X-ray tube 101 and the detector 103 are rotatably mounted on the rotating part 1. A rotary joint 3 serves as an electrical connection between the rotating part 1 and the stationary part 2. By means of this, the high electrical power for energizing the X-ray tube 101 is transmitted in a direction towards the rotating part 1, and simultaneously the raw data of the image are transmitted in the opposite direction. A communication of control information in both directions is provided in parallel with this. An evaluation and control unit 106 serves for operation of the computer tomograph, and also for displaying generated images. Communication with the computer tomograph is effected via a bidirectional link 105.

Figure 2:
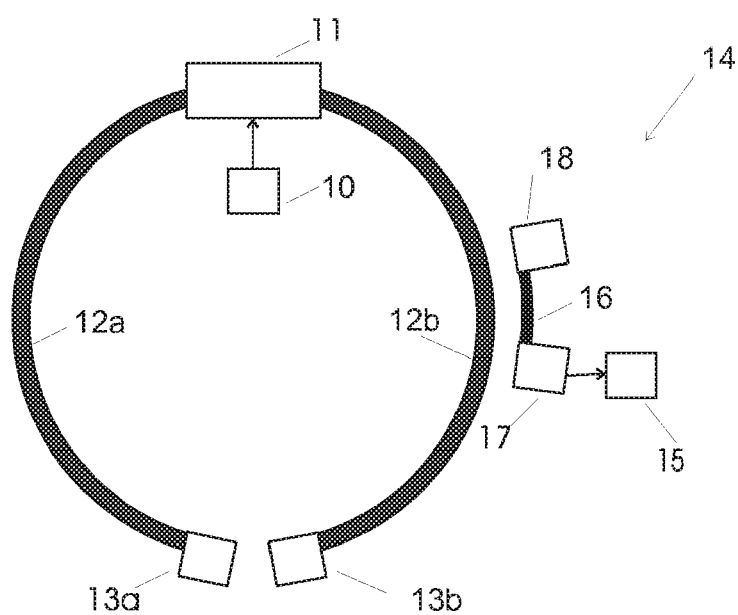
FIG. 2 shows details of an example of a device in accordance with the invention.

FIG. 2 shows details of an example of a device in accordance with the invention. A transmitter 10, for example the X-ray detector of a computer tomograph on its rotating gantry, serves to emit high-frequency signals into a first conductor coupler 11 and from there into a divided conductor structure 12a, 12b. In the simplest case, this first conductor coupler may be a galvanic connection, or also a capacitor, a filter, a directional coupler etc. The ends of the branches of the divided conductor structure are closed by means of terminations 13a, 13b so as to be substantially free from reflection. A receiver 15 is disposed to be movable relative to this, or on a stationary part of the gantry, to receive the signals tapped off from a receiver coupler 14. The receiver coupler 14 couples the field in the vicinity of the first conductor structure on the transmitter side without contact, and may be constructed, for example, using strip-conductor technology to form a conductor structure 16. In the case of a strip conductor, this coupler is preferably closed off by means of a termination 18 to be free from reflection. The connection to the receiver 15 may be effected via a conductor coupler 17, or also via direct galvanic or capacitive contact.

Figure 3:
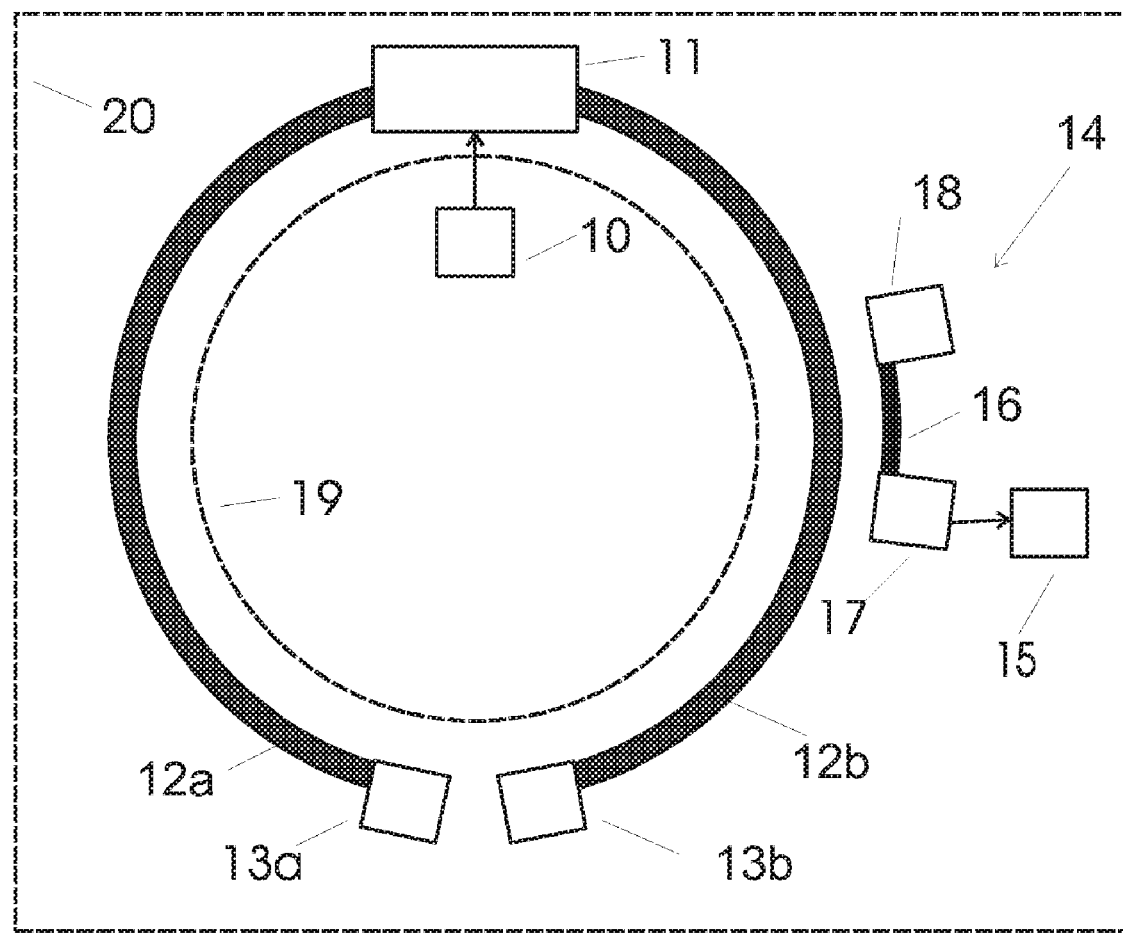
FIG. 3 shows the details as in FIG. 2, but with an added ring-shaped or annular absorber antenna and a rectangular absorber antenna.

FIG. 3 shows details of an example of a device in accordance with the invention, which have already been shown in FIG. 2 and described above in connection with FIG. 2. In addition, however, a ring-shaped or annular absorber antenna 19 and a rectangular absorber antenna 20 serve to reduce interference radiation. These antennas may be provided as alternatives, or simultaneously.

Figure 4:
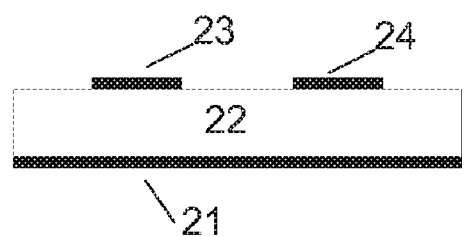
FIG. 4 shows a cross-section of a typical conductor arrangement.

FIG. 4 shows a cross-section of a typical conductor arrangement. A first conductor 23 and a second conductor 24 are disposed on a dielectric 22. A screen surface 21 is provided on the lower side. Usually the two conductors 23 and 24 are operated with differential signals. This results in only little radiation in the far field. The conductor arrangement is usually closed off at its ends to be free from reflection. With this, normally no resonances can arise on the conductors themselves. However, the entire arrangement itself, consisting of conductors and screen surfaces, is capable of resonance.

The invention claimed is:

1. Device for transmitting data between a rotating part and a stationary part of a computer tomograph, in which the rotating part comprises:
   at least one data source;
   a conductor structure; and
   at least one first transmitter for energizing the conductor structure;
   wherein the stationary part comprises:
      at least one data sink for evaluating data;
      at least one receiver; and
      a receiver coupler for tapping off signals from the conductor structure and supplying the signals to the at least one receiver; and
   wherein a resonance frequency of at least one of the rotating part and the conductor structure, and a spectral distribution of data of the at least one transmitter, are matched to each other.

2. Device according to claim 1, wherein the resonance frequency of at least one of the rotating part and the conductor structure are dimensioned to be within a frequency range in which high-frequency energy emitted by the at least one transmitter has a minimum value.

3. Device according to claim 1, wherein regions in the vicinity of the conductor structure comprise a dielectric.

4. Device according to claim 1, wherein a length of the conductor structure is dimensioned to correspond to approximately a whole-number multiple of one half of a wavelength of a predetermined frequency in which preferably high-frequency energy emitted by the at least one transmitter has a minimum value.

5. Device according to claim 1, wherein a length of the conductor structure with short-circuited conductor ends is dimensioned to correspond to approximately a whole-number multiple of a quarter of a wavelength of a predetermined frequency in which preferably high-frequency energy emitted by the at least one transmitter has a minimum value.

6. Device for transmitting data between a rotating part and a stationary part of a computer tomograph, in which the rotating part comprises:
   at least one data source;
   a conductor structure; and
   at least one first transmitter for energizing the conductor structure;
   wherein the stationary part comprises:
      at least one data sink for evaluating data;
      at least one receiver; and
      a receiver coupler for tapping off signals from the conductor structure and supplying the signals to the at least one receiver; and
   wherein at least one of a dielectric and ferromagnetic material that is attended by losses is provided to be at least one of laterally of and below the conductor structure.

7. Device for transmitting data between a rotating part and a stationary part of a computer tomograph, in which the rotating part comprises:
   at least one data source;

a conductor structure; and at least one first transmitter for energizing the conductor structure;

wherein the stationary part comprises:

at least one data sink for evaluating data;

at least one receiver; and a receiver coupler for tapping off signals from the conductor structure and supplying the signals to the at least one receiver; and wherein ends of the conductor structure are interconnected so as to be attended by losses, in particular with an ohmic resistance.

8. Device for transmitting data between a rotating part and a stationary part of a computer tomograph, in which the rotating part comprises:

at least one data source;

a conductor structure; and at least one first transmitter for energizing the conductor structure;

wherein the stationary part comprises:

at least one data sink for evaluating data;

at least one receiver; and a receiver coupler for tapping off signals from the conductor structure and supplying the signals to the at least one receiver; and wherein a transmission signal of the at least one transmitter is folded with a bit sequence that is selected so that its spectrum corresponds to a given transmission spectrum.

9. Device for transmitting data between a rotating part and a stationary part of a computer tomograph, in which the rotating part comprises:

at least one data source;

a conductor structure; and at least one first transmitter for energizing the conductor structure;

wherein the stationary part comprises:

at least one data sink for evaluating data;

at least one receiver; and a receiver coupler for tapping off signals from the conductor structure and supplying the signals to the at least one receiver;

wherein at least one absorber antenna for absorbing undesired interference is provided in a vicinity of the conductor structure.

10. Device according to claim 9, wherein at least one of the absorber antennas is designed as a closed conductor loop, and is preferably attended by losses.

11. Device according to claim 9, wherein at least one of the absorber antennas is designed to be optionally round or rectangular.

12. Device according to claim 9, wherein at least one of the absorber antennas comprises at least one material that is attended by losses.

13. Device according to claim 9, wherein at least one of the absorber antennas comprises at least one attenuating resistor.

14. Device according to claim 9, wherein at least one of the absorber antennas comprises at least one of a series inductance and a series capacity.

15. Device according to claim 9, wherein at least one of the absorber antennas comprises at least one of a parallel inductance and a parallel capacity to a common ground.

16. Device according to claim 9, wherein at least one of the absorber antennas is tuned to a predetermined frequency.

17. Device according to claim 9, wherein a plurality of absorber antennas are tuned to a plurality of predetermined frequencies.

18. Device according to claim 9, wherein at least one of the absorber antennas is configured to be of rectangular shape, and side lengths are whole-number multiples of $\lambda/8$ of a frequency to be attenuated.

19. Device according to claim 9, wherein at least one of the absorber antennas is configured to be of circular shape, and a circumference is a whole-number multiple of $\lambda/8$ of a frequency to be attenuated.

20. Device according to claim 9, wherein at least one of the absorber antennas comprises a plurality of windings.

* * * * *